(12) United States Patent
Cojbasic

(10) Patent No.: US 7,442,176 B2
(45) Date of Patent: Oct. 28, 2008

(54) DYNAMIC CERVICAL SUPPORT BRACE

(76) Inventor: Milun Cojbasic, Milana Jonvanovica St. 57/1, 3200 Cacak (YU)

( * ) Notice: Subject to any disclaimer, the term of this patent is extended or adjusted under 35 U.S.C. 154(b) by 443 days.

(21) Appl. No.: 11/323,972

(22) Filed: Dec. 29, 2005

(65) Prior Publication Data

US 2007/0156071 A1      Jul. 5, 2007

(51) Int. Cl.
*A61F 5/00* (2006.01)
(52) U.S. Cl. .................................. 602/18; 128/DIG. 23
(58) Field of Classification Search ............. 602/17–19; 128/DIG. 23
See application file for complete search history.

(56) References Cited

U.S. PATENT DOCUMENTS

| | | | |
|---|---|---|---|
| 4,518 A | 5/1846 | Sullivan | |
| 9,826 A | 7/1853 | Abbe | |
| 709,055 A | 11/1902 | Sheldon | |
| 954,005 A | 4/1910 | Roth | |
| 1,043,648 A | 11/1912 | Weaver | |
| 1,722,205 A | 7/1929 | Freund | |
| 1,803,556 A | 5/1931 | Nugent | |
| 1,930,440 A * | 10/1933 | Longfellow | 602/18 |
| 2,060,173 A | 11/1936 | Buschenfeldt | |
| 2,492,383 A | 12/1949 | Jones | |
| 2,807,260 A * | 9/1957 | Teufel | 602/17 |
| 2,820,455 A | 1/1958 | Hall | |
| 2,828,737 A | 4/1958 | Hale | |
| 3,177,869 A | 4/1965 | Bartels | |
| 3,364,926 A * | 1/1968 | Alderson | 602/18 |
| 3,596,655 A | 8/1971 | Corcoran | |
| 3,601,123 A | 8/1971 | McFarland | |
| 3,675,646 A | 7/1972 | Corcoran | |
| 3,771,513 A | 11/1973 | Velazquez | |
| 3,776,224 A | 12/1973 | McFarland | |
| 3,945,376 A | 3/1976 | Kuehnegger | |
| 3,957,040 A | 5/1976 | Calabrese | |
| 4,383,523 A | 5/1983 | Schurman | |
| 4,539,979 A | 9/1985 | Bremer | |
| 4,620,530 A | 11/1986 | Lanier et al. | |
| 4,715,362 A | 12/1987 | Scott | |
| 4,732,144 A | 3/1988 | Cunanan | |
| 4,735,196 A | 4/1988 | Krag et al. | |
| 4,807,605 A | 2/1989 | Mattingly | |
| 4,827,915 A | 5/1989 | Gorsen | |
| 4,951,655 A | 8/1990 | MacMillan et al. | |
| 5,046,490 A | 9/1991 | Young et al. | |
| 5,088,482 A | 2/1992 | McGuinness | |
| 5,171,296 A | 12/1992 | Herman | |
| 5,195,947 A | 3/1993 | Bode | |
| 5,242,377 A | 9/1993 | Boughner et al. | |
| 5,259,833 A | 11/1993 | Barnett | |

(Continued)

*Primary Examiner*—Michael Brown
(74) *Attorney, Agent, or Firm*—Philip H. Gottfried; Amster, Rothstein & Ebenstein LLP

(57) ABSTRACT

A cervical support brace including an upper U-shaped support member having a first support prong and a second support prong and a lower U-shaped support member having a first support prong and a second support prong. A first linkage member connects the first support prong of the upper U-shaped support member with the first support prong of the lower U-shaped support member. A second linkage member connects the second support prong of the upper U-shaped support member with the second support prong of the lower U-shaped support member. The linkage members allow for a dynamic range of motion of the cervical support brace when worn.

11 Claims, 6 Drawing Sheets

U.S. PATENT DOCUMENTS

| | | |
|---|---|---|
| 5,782,783 A | 7/1998 | Young et al. |
| 6,267,741 B1 | 7/2001 | Lerman |
| 6,315,746 B1 | 11/2001 | Garth et al. |
| 6,681,770 B1 | 1/2004 | Dreher |
| 6,770,047 B2 | 8/2004 | Bonutti |
| 7,128,724 B2 * | 10/2006 | Marsh .................. 602/18 |
| 2003/0220594 A1 | 11/2003 | Halvorson et al. |
| 2004/0204666 A1 | 10/2004 | Marsh |

* cited by examiner

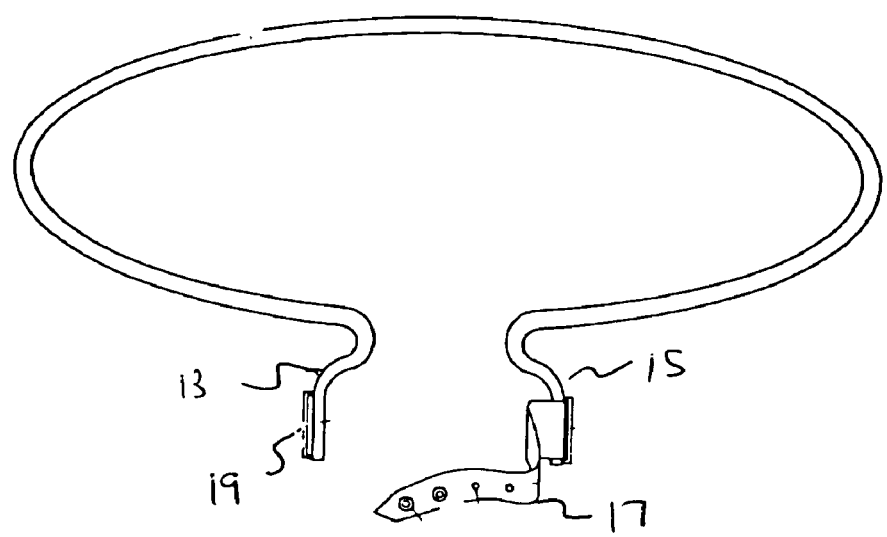
Figure 2
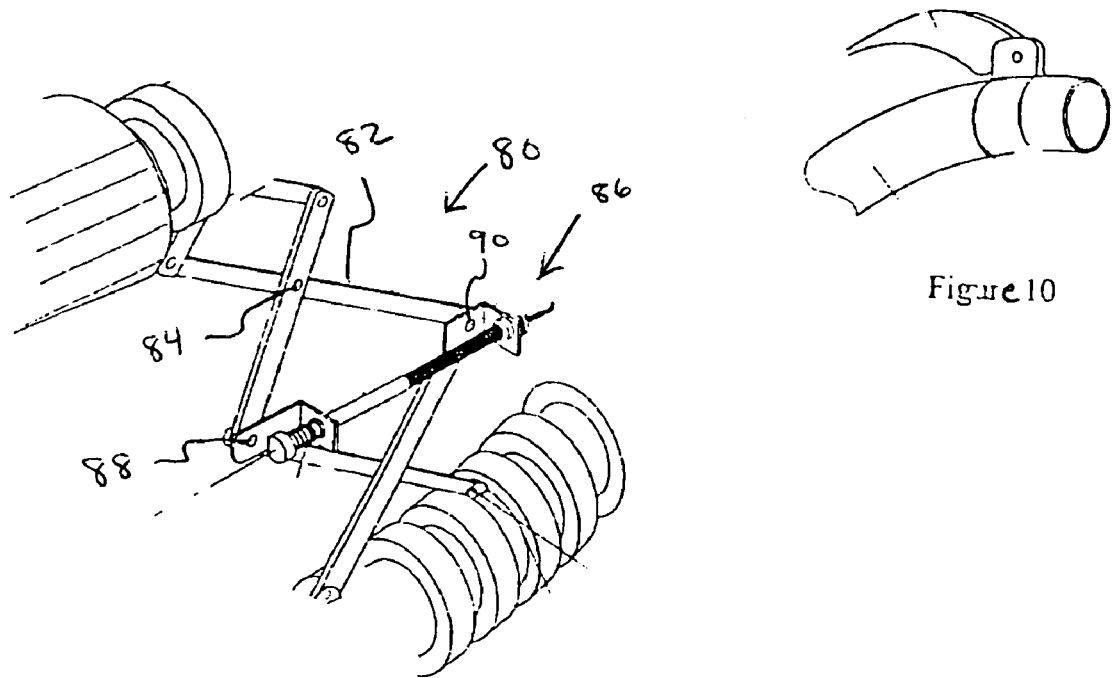
Figure 10
Figure 3

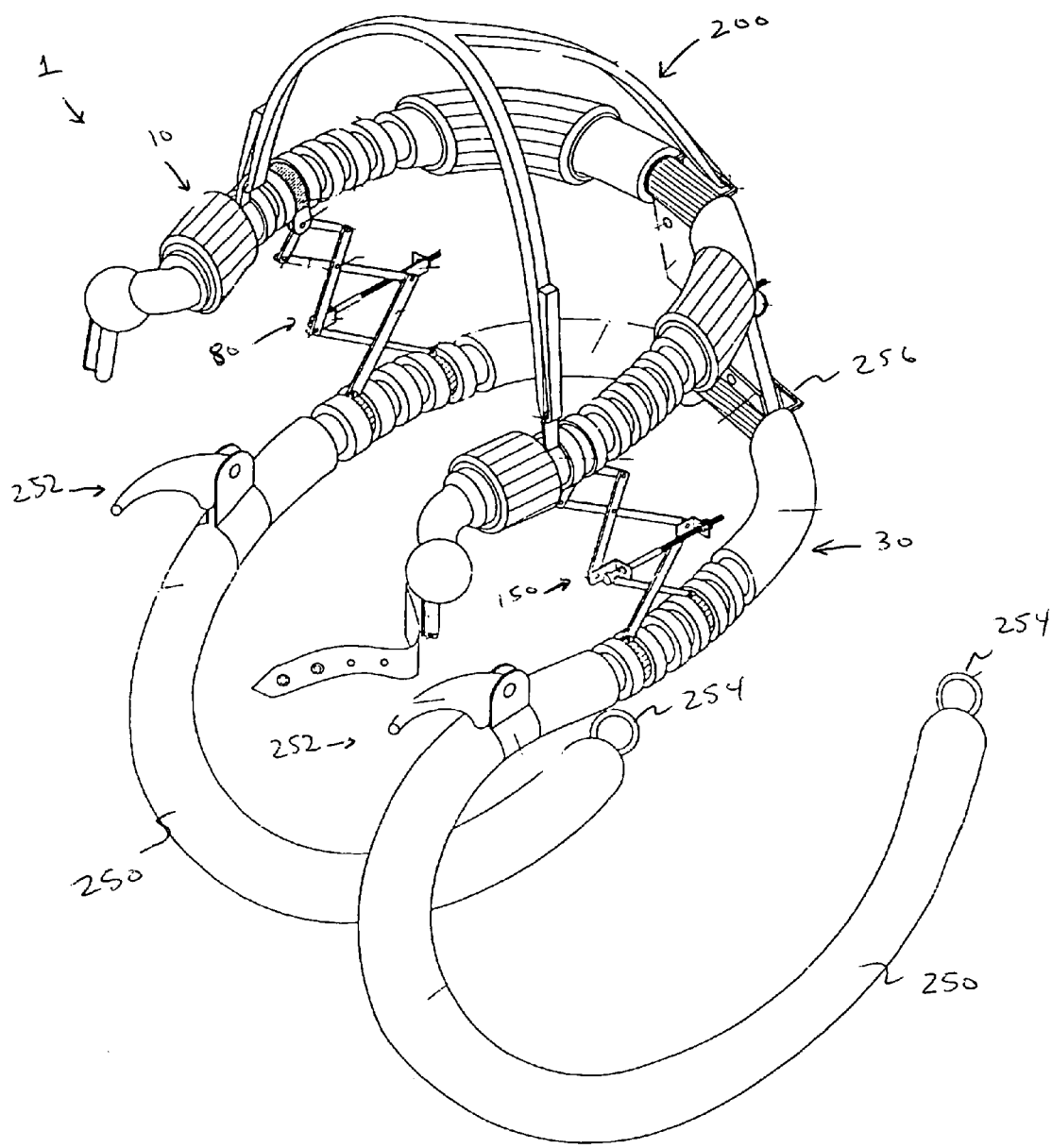
Figura 9

DYNAMIC CERVICAL SUPPORT BRACE

CROSS-REFERENCE TO RELATED APPLICATION

This application claims the benefit of Serbia and Montenegro Application No. P-1163/04, filed Dec. 30, 2004.

TECHNICAL FIELD

The present invention relates to devices and methods for providing cervical support.

BACKGROUND

It is common, in treating a patient with a fractured vertebra or other neck injury, to immobilize the neck for proper healing by supporting the patient's head with a support brace which renders it relatively immovable. The head of the patient is thus maintained in a fixed position or support relative to the patient's body, which often results in weakening of the neck muscles from lack of exercise and reduced circulation. The rigidity of the these known devices also are a great discomfort to the patient. Further, when the patient's head is immobilized, the patient may suffer from eye strain in attempting to view objects outside of his/her field of vision. Also, known neck braces often do not have built-in means for cushioning the head and neck against physical shock resulting from an accident or the like, while still allowing the patient some range-of-motion.

Accordingly, there is a need for a neck brace that provides adequate support to the head and neck, while still providing the patient with some range-of-motion for added comfort and to reduce muscle atrophy.

SUMMARY OF THE INVENTION

A cervical support brace according to an exemplary embodiment of the invention includes an upper U-shaped support member having a first support prong and a second support prong and a lower U-shaped support member having a first support prong and a second support prong. A first linkage member connects the first support prong of the upper U-shaped support member with the first support prong of the lower U-shaped support member. A second linkage member connects the second support prong of the upper U-shaped support member with the second support prong of the lower U-shaped support member. Each of the first and second linkage members includes an adjustment mechanism disposed between two parallel pivot points within each of the first and second linkage members. The adjustment mechanism includes a first bracket, a second bracket, a bolt, a spring and a adjustable nut. A first portion of the first bracket is rotationally fixed to one of the two parallel pivot points. A second portion of the first bracket has a through-hole. A first portion of the second bracket is rotationally fixed to the other of the two parallel pivot points. A second portion of the second bracket has a through-hole. The bolt extends through the through-hole of the first bracket and the through-hole of the second bracket. The bolt has a head and a threaded end portion. The spring is disposed between the head of the bolt and the second portion of the first bracket. The adjustable nut is disposed on the threaded end of the bolt. The nut has a circumferential groove. The second portion of the second bracket is partially disposed within the circumferential groove, such that location of the nut along the threaded end of the bolt may be adjusted to expand or contract the cervical support brace.

These and other features of this invention are described in, or are apparent from, the following detailed description of various exemplary embodiments of this invention.

BRIEF DESCRIPTION OF THE DRAWINGS

Various exemplary embodiments of this invention will be described in detail, with reference to the following figures, wherein:

FIG. 2 shows an attachment mechanism used with the dynamic cervical support brace of FIG. 1;

FIG. 3 shows a linkage mechanism used with the dynamic cervical support brace of FIG. 1;

FIG. 9 shows the dynamic cervical support brace of FIG. 1 including shoulder extensions and a head brace; and FIG. 10 shows a clamp mechanism used to attach shoulder extensions to the cervical support brace of FIG. 1.

DETAILED DESCRIPTION OF PREFERRED EMBODIMENTS

The present invention is a dynamic cervical support brace that provides the wearer with a limited range of head and neck motion without complete immobilization. The cervical support brace of the present invention is readily extended or contracted, thereby allowing adjustment of the brace for more mobility as the neck injury heals, which in turn prevents complications associated with complete immobilization, such as muscle atrophy.

Figure 1:
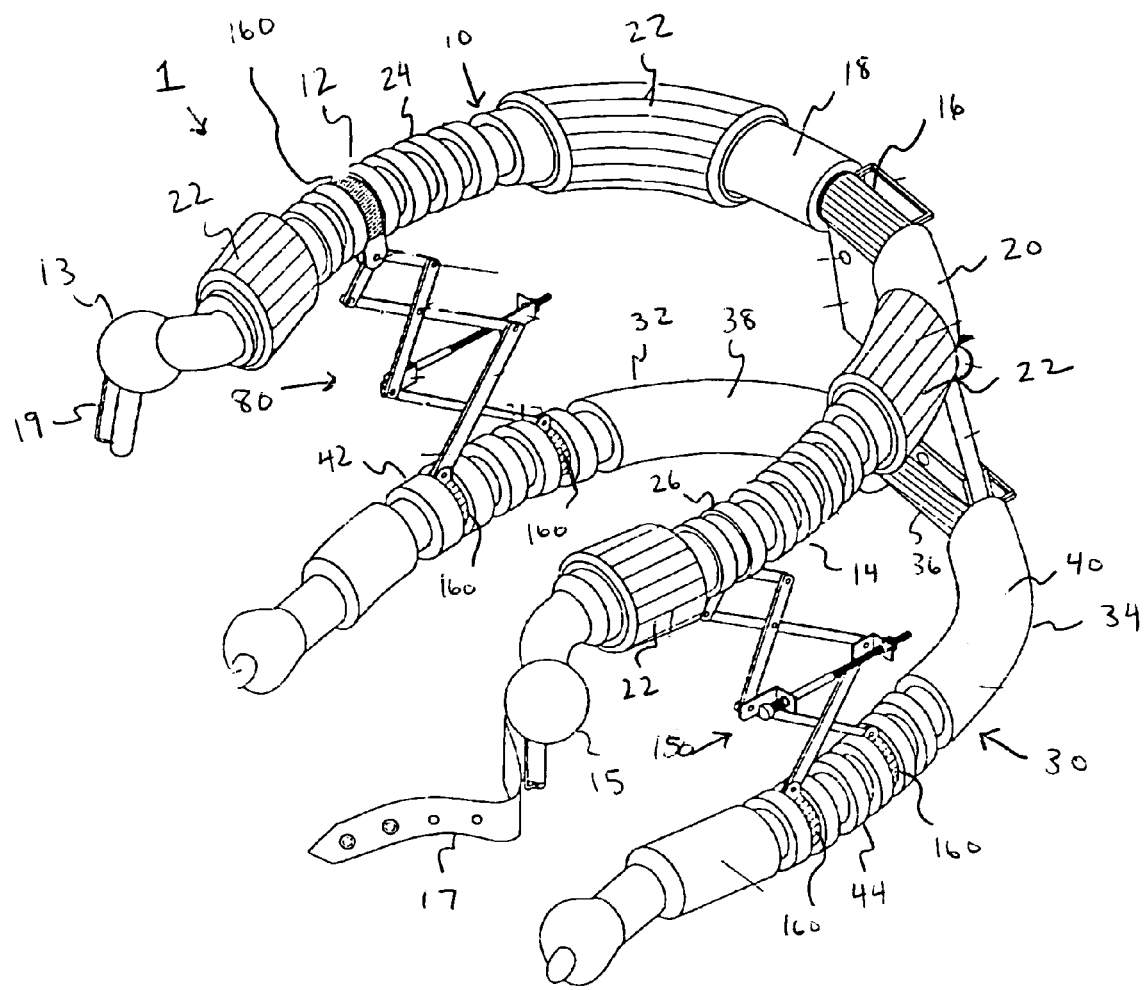
FIG. 1 shows a dynamic cervical support brace according to an exemplary embodiment of the invention'

FIG. 1 shows a dynamic cervical support brace, generally designated by reference numeral 1, according to an exemplary embodiment of the present invention. The cervical support brace 1 includes an upper U-shaped support member, generally designated by reference numeral 10, and a lower U-shaped support member, generally designated by reference numeral 30. The upper U-shaped support member 10 includes a first prong 12 and a second prong 14, and the lower U-shaped support member 30 also includes a first prong 32 and a second prong 34. The upper U-shaped support member 10 includes a core member 16, and a first rubber sleeve 18 disposed around the core member 16 at the first prong 12 and a second rubber sleeve 20 disposed around the core member 16 at the second prong 14. Likewise, the lower U-shaped support member 30 includes a core member 36, and a first rubber sleeve 38 disposed around the core member 36 at the first prong 32 and a second rubber sleeve 40 disposed around the core member 36 at the second prong 34. The core members 16 and 36 are preferably made of a semi-rigid material, such as metal or plastic. Additional cushioning may be provided on the upper U-shaped support member, such as pads 22. The rubber sleeves 18, 20, 38 and 40 preferably include a plurality of ribs 24, 26, 42 and 44, respectively.

As shown in FIG. 2, the first and second prongs 12 and 14 of the upper U-shaped support member 10 terminate in end portions 13 and 15, respectively, that are preferably bent outwardly and downwards. An adjustable fastening mechanism is placed between the end portion 13 and 15 so that the cervical support 1 can be properly secured under the jaw of the wearer. For example, the fastening mechanism may include a belt 17 fixed to the end portion 15 that cooperates with a buckle 19 fixed to the end portion 13. Any other suitable fastening mechanism may be used with the present invention.

Figure 5:
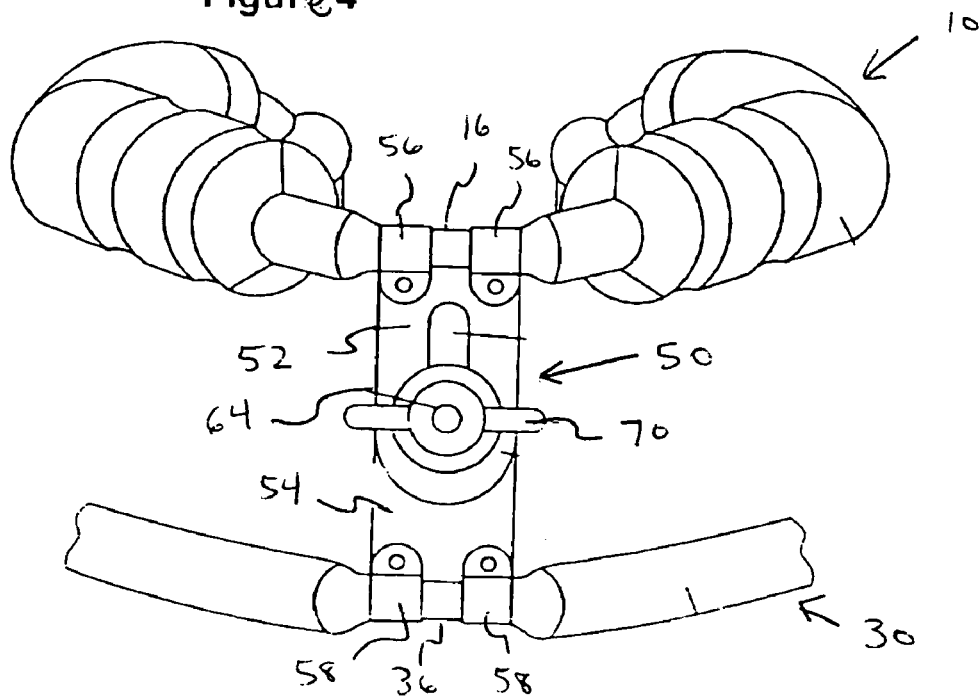
FIG. 5 shows a locking mechanism used with the dynamic cervical support brace of FIG. 1.
Figure 6:
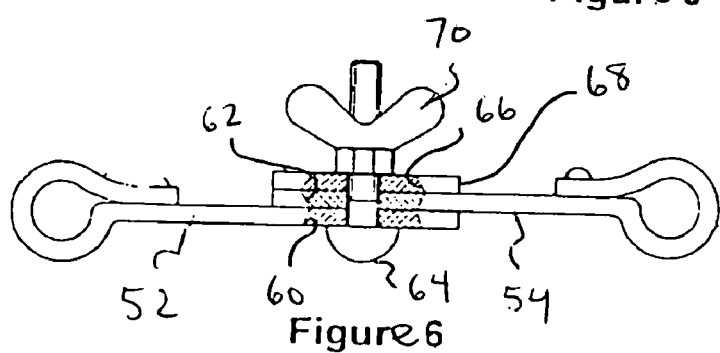
FIG. 6 is a cross-sectional view of the locking mechanism of FIG. 5.

As shown most clearly in FIGS. 5 and 6, an adjustable locking mechanism, generally designated by reference numeral 50, is disposed between the upper and lower U-shaped support members 10 and 30 at the back portion of the cervical support brace 1. The locking mechanism 50 includes a first locking plate 52 fixed to the core member 16 of the upper U-shaped support member 10 and a second locking plate 54 fixed to the core member 36 of the lower U-shaped support member 30. In this regard, the first locking plate 52 may include extending portions that are bent in the form of loops 56 around the core member 16 of the upper U-shaped support member 10. Thus, the upper U-shaped support member 10 is free to pivot within the loops 56. Likewise, the second locking plate 54 may include extending portions that are bent in the form of loops 58 around the core member 36 of the lower U-shaped support member 30. Thus, the lower U-shaped support member 30 is free to pivot within the loops 58.

Both the first and second locking plates 52 and 54 include substantially vertically extending through-holes 60 and 62, respectively. A locking bolt 64 extends through the through-holes 60 and 62, and also through a through-hole 66 formed in spacer 68. The locking bolt 64 may be locked into position using a wing nut 70. In this way, the vertical spacing between the upper and lower U-shaped support members 10 and 30 may be adjusted by fixing the first and second locking plates 52 and 54 into desired relative positions using the locking bolt 64 and wing nut 70.

As shown in FIGS. 1 and 3, a first adjustable linkage member, generally designated as reference numeral 80, connects the first prong 12 of the first U-shaped support member 10 with the first prong 32 of the lower U-shaped support member 30, and a second adjustable linkage member, generally designated by the reference numeral 150, connects the second prong 14 of the first U-shaped support member 10 with the second prong 34 of the lower U-shaped support member 30. Multiple collars 160 may be used to pivotally attach the first and second adjustable linkage members 80 and 150 to the corresponding prongs 12, 32, 14, 34. The collars 160 are preferably disposed around the rubber sleeves 18, 38, 20, 40 between pairs of ribs 24, 26, 42 and 44. The first and second adjustable linkage members 80 and 150 have equivalent structure, and therefore only the first adjustable linkage member 80 is described below.

Figure 4:
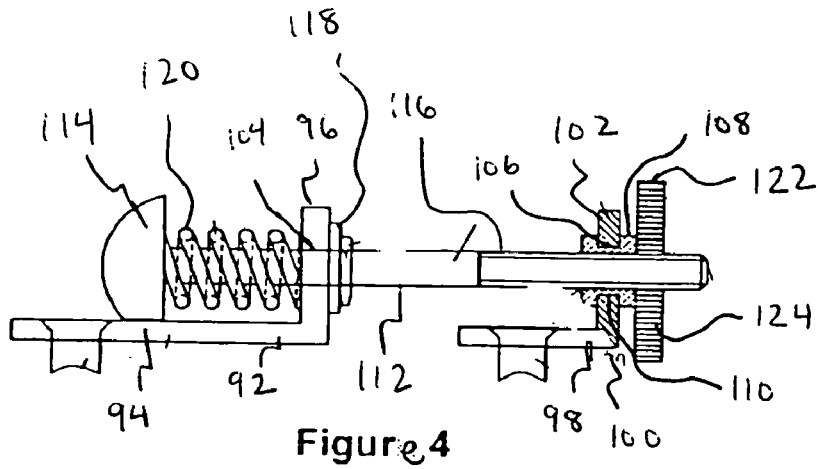
FIG. 4 shows an adjustment mechanism used with the dynamic cervical support brace of FIG. 1.

The first adjustable linkage member 80 includes a plurality of pivotally linked bars 82 arranged in a truss-like configuration. The bars 82 may be pivotally linked by, for example, rivets 84. As shown in FIGS. 3 and 4, an adjustment mechanism, generally designated as reference numeral 86, connects and extends between a first pivot point 88 and a parallel second pivot point 90 within the first adjustable linkage member 80. The adjustment mechanism 86 includes L-shaped first and second brackets 92 and 98. The first bracket 92 has a first portion 94 and a second portion 96 extending perpendicular to the first portion 94. The first portion 94 of the first bracket 92 is pivotally attached to the first pivot point 88. The second bracket 98 has a first portion 100 and a second portion 102 extending perpendicular to the first portion 100. The first portion 100 of the second bracket 98 is pivotally attached to the second pivot point 90.

As shown in FIG. 4, the second portion 96 of the first bracket 92 has a through-hole 104 and the second portion 102 of the second bracket 98 has a through-hole 106. An adjustment nut 108 is disposed within the through-hole 106 of the second bracket 98. The adjustment nut 108 includes an outer circumferential groove 110. The second portion 102 of the second bracket 98 is partially disposed within the circumferential groove 110, so that the second portion 102 is essentially fastened to the adjustment nut 108.

The adjustment mechanism 86 also includes an adjustment bolt 112 having a bolt head 114 and a threaded end portion 116. The adjustment bolt 112 extends through the through-holes 104 and 106, such that the adjustment nut 108 is threadedly engaged with the threaded end portion 116 of the adjustment bolt 112 within the through-hole 106 of the second bracket 98. The adjustment bolt 112 is free to move within the through-hole 104 formed in the second portion 96 of the first bracket 92. A wedge 118 is formed on the adjustment bolt 112 to limit the inwards axial movement of the second portion 96 of the first bracket 92 when the cervical support brace 1 is extended during use. A spring 120 is disposed between the bolt head 114 and the second portion 96 of the first bracket 92 to limit the outwards axial movement of the second portion 96 of the first bracket 92 when the cervical support brace 1 is contracted during use.

The adjustment nut 108 preferably includes a grip flange 122 having a plurality of ribs 124. In operation, the dynamic cervical support brace 1 can be expanded or contracted by turning the adjustment nut 108 using the grip flange 120. In particular, threading the adjustment nut 108 inwards towards the adjustment bolt head 114 will result in expansion of the dynamic cervical support brace 1, while threading the adjustment nut outwards away from the adjustment bolt head 114 will result in contraction of the dynamic cervical support brace 1. Because the adjustment bolt 112 is free to move within the through-hole 104 formed in the second portion 96 of the first bracket 92, the cervical support brace 1 provides a range of motion as limited by the wedge 118 and spring 120, thereby providing some mobility to the wearer's head and neck region.

Figure 7:
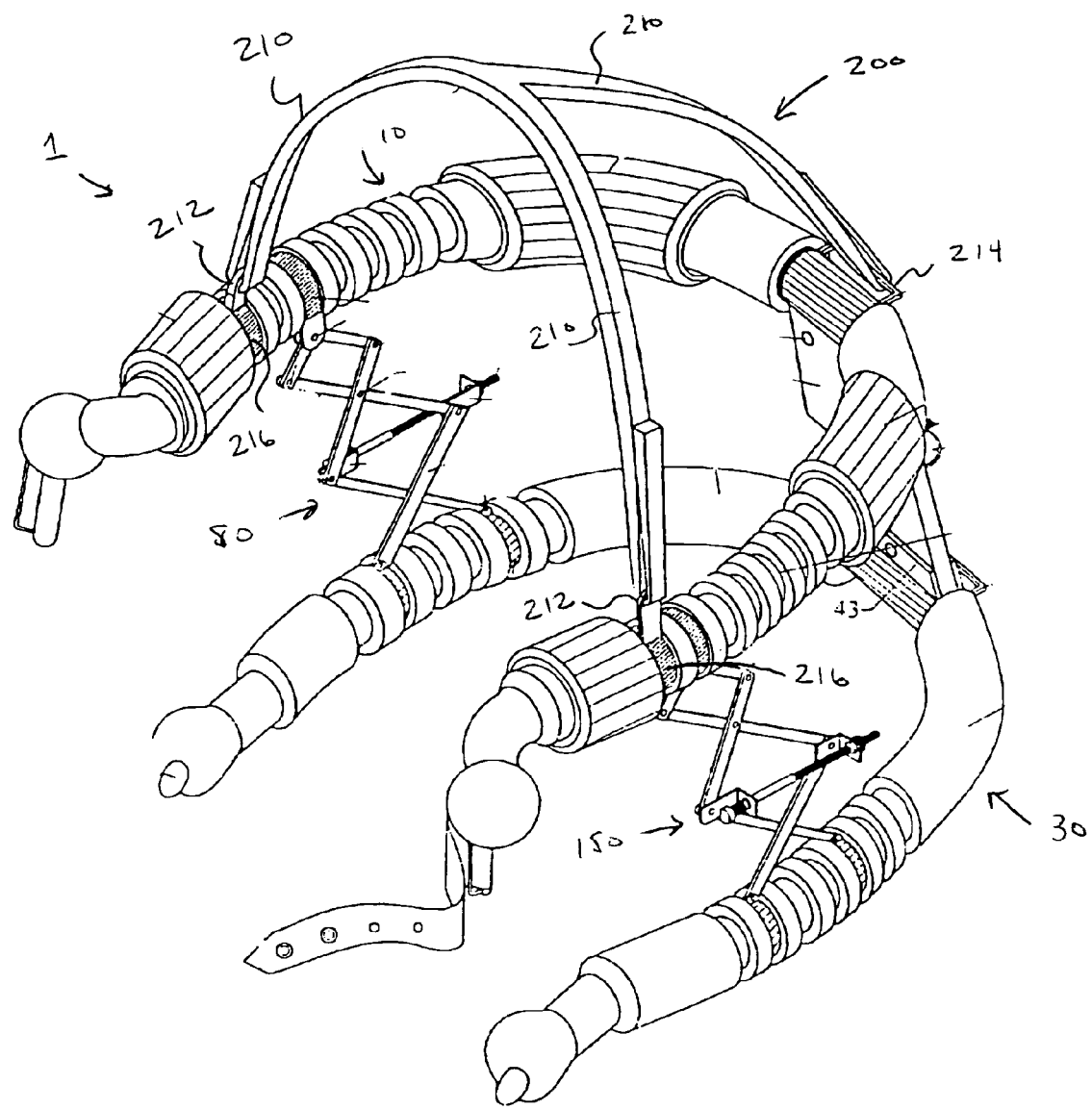
FIG. 7 shows the dynamic cervical support brace of FIG. 1 including a head brace.

As shown in FIGS. 7 and 9, the dynamic cervical support brace 1 may also include a head brace, generally designated by reference numeral 200. The head brace 200 includes a number of relatively stiff straps 210 that form a cage-like structure around the wearer's head. The straps 210 are attached to the upper U-shaped support member 10 by clasps 212 formed on the first and second prongs 12 and 14 and a buckle 214 extending from the back portion of the upper U-shaped support member 10. The clasps 212 may extend from collars 216 disposed around the upper U-shaped support member 10.

Figure 8:
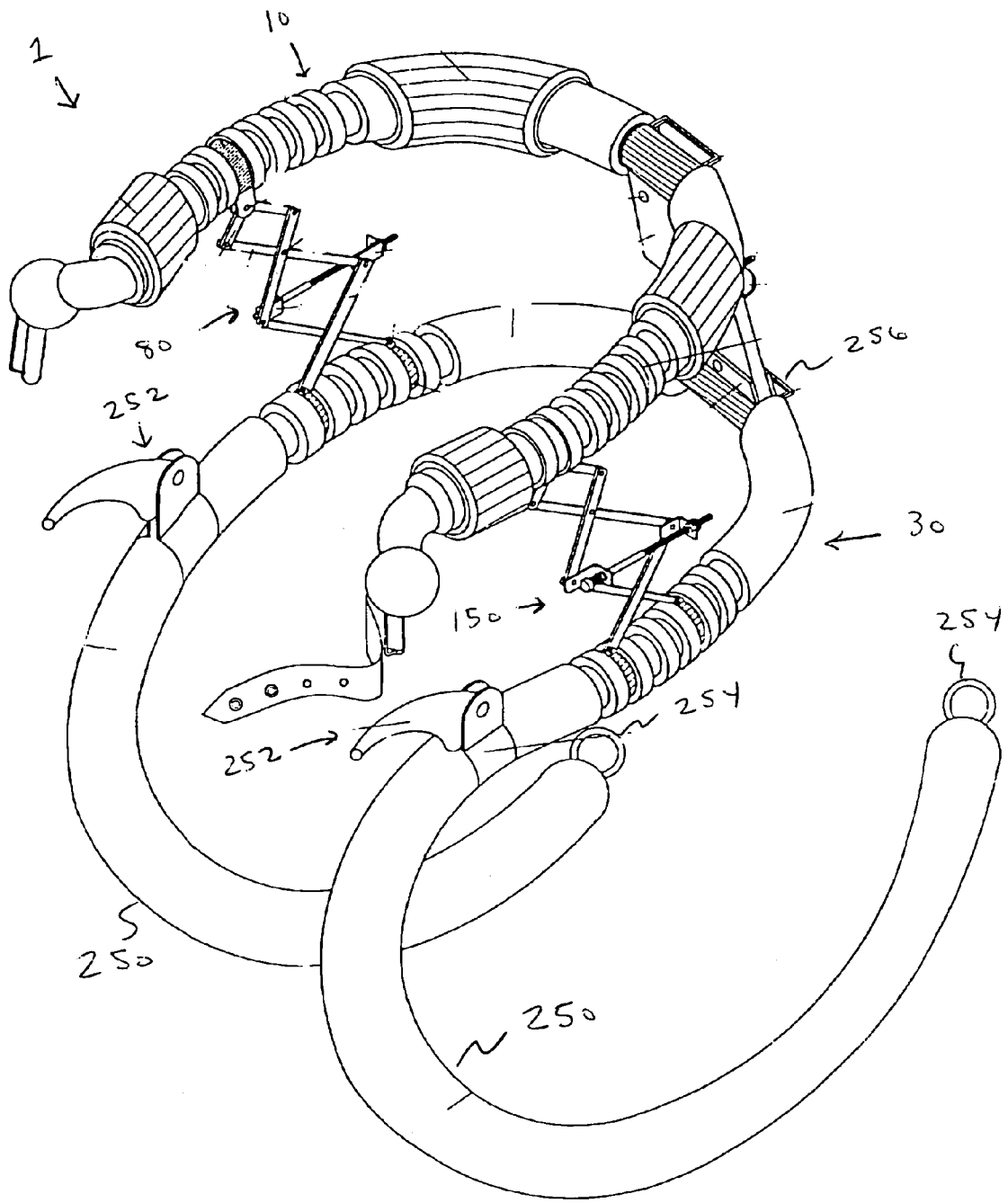
FIG. 8 shows the dynamic cervical support brace of FIG. 1 including shoulder extensions.

As shown in FIGS. 8 and 9, the dynamic cervical support member 1 may also include shoulder extensions 250. The shoulder extensions 250 may be attached to the ends of the first and second prongs 32 and 34 of the lower U-shaped support member 30 by, for example, clamp elements 252, as shown in FIG. 10. The shoulder extensions 250 are preferably formed of a bendable material, such as, for example, rubber or metal, so that they can be adjusted to extend under the wearer's shoulders. The end portions of the shoulder extensions 250 include loops 254 for attachment to straps (not shown) which can extend and attach to buckle 256 extending from the back portion of the lower U-shaped support member 30.

Now that the preferred embodiments have been shown and described in detail, various modifications and improvements thereon will be readily apparent to those skilled in the art. Accordingly, the spirit and scope of the present invention is to be construed broadly and be limited only by the appended claims, and not by the foregoing specification.

What is claimed is:

1. A cervical support brace comprising:
   an upper U-shaped support member having a first support prong and a second support prong;
   a lower U-shaped support member having a first support prong and a second support prong;
   a first linkage member that connects the first support prong of the upper U-shaped support member with the first support prong of the lower U-shaped support member; and
   a second linkage member that connects the second support prong of the upper U-shaped support member with the second support prong of the lower U-shaped support member;
   each of the first and second linkage members comprising an adjustment mechanism disposed between two parallel pivot points within each of the first and second linkage members, the adjustment mechanism comprising:
      a first bracket, a first portion of the first bracket being rotationally fixed to one of the two parallel pivot points, a second portion of the first bracket having a through-hole;
      a second bracket, a first portion of the second bracket being rotationally fixed to the other of the two parallel pivot points, a second portion of the second bracket having a through-hole;
      a bolt extending through the through-hole of the first bracket and the through-hole of the second bracket, the bolt having a head and a threaded end portion;
      a spring disposed between the head of the bolt and the second portion of the first bracket; and
      an adjustable nut disposed on the threaded end of the bolt, the nut having a circumferential groove, the second portion of the second bracket being partially disposed within the circumferential groove, such that location of the nut along the threaded end of the bolt may be adjusted to expand or contract the cervical support brace.

2. The cervical support brace of claim 1, further comprising a separate sleeve disposed around each one of the first and second support prongs of the upper and lower U-shaped support members.

3. The cervical support brace of claim 2, further comprising at least one collar disposed around each of the sleeves for attaching the first and second linkage members to the corresponding support prongs.

4. The cervical support brace of claim 3, wherein the sleeves comprise a plurality of ribs, and the at least one collar disposed around each sleeve is disposed between a pair of the plurality of ribs of the sleeve.

5. The cervical support brace of claim 1, wherein the bolt comprises a wedge that limits the axial movement of the first bracket along the bolt when the cervical support brace is extended by a wearer.

6. The cervical support brace of claim 1, further comprising an adjustable locking mechanism comprising:
   a first locking plate pivotally attached to the upper U-shaped support member, the first locking plate having a substantially vertically extending through-hole;
   a second locking plate pivotally attached to the lower U-shaped support member, the second locking plate having a substantially vertically extending through-hole that coincides with the through-hole formed in the first locking plate;
   a locking bolt extending though the through-holes formed in the first and second locking plates; and
   a nut threadedly engageable with the locking bolt to lock the first and second locking plates in relative position.

7. The cervical support brace of claim 1, further comprising a fastening mechanism that fastens together the first and second prongs of the upper U-shaped support member.

8. The cervical support brace of claim 7, wherein the fastening mechanism comprises a belt and buckle arrangement.

9. The cervical support brace of claim 1, further comprising a head brace extending from the upper U-shaped support member.

10. The cervical support brace of claim 9, wherein the head brace comprises a plurality of straps extending from the upper U-shaped support member.

11. The cervical support brace of claim 1, further comprising a first shoulder extension extending from the first prong of the lower U-shaped support member and a second shoulder extension extending from the second prong of the lower U-shaped support member.

* * * * *